US006172280B1

(12) United States Patent
Burr et al.

(10) Patent No.: US 6,172,280 B1
(45) Date of Patent: Jan. 9, 2001

(54) BACTERIAL RESISTANCE IN GRAPEVINE

(75) Inventors: Thomas J. Burr; Dennis Gonsalves, both of Geneva, NY (US); Sheng-Zhi Pang, Ellisville, MO (US)

(73) Assignee: Cornell Research Foundation, Inc., Ithaca, NY (US)

( * ) Notice: Under 35 U.S.C. 154(b), the term of this patent shall be extended for 0 days.

(21) Appl. No.: 09/173,416

(22) Filed: Oct. 15, 1998

Related U.S. Application Data
(60) Provisional application No. 60/062,246, filed on Oct. 17, 1997.

(51) Int. Cl.[7] ............................. C12N 5/04; C12N 15/82; C12N 15/84; C12N 15/90; A01H 5/00

(52) U.S. Cl. ......................... 800/279; 435/419; 435/468; 800/288; 800/301

(58) Field of Search .................................... 435/410, 419, 435/468, 430.1, 69.1; 800/278, 279, 288, 295, 298, 301

(56) References Cited

U.S. PATENT DOCUMENTS

| | | | |
|---|---|---|---|
| 4,315,029 | 2/1982 | Mori et al. | 424/304 |
| 5,187,073 | 2/1993 | Goldman et al. | 435/469 |
| 5,232,940 | 8/1993 | Hatton et al. | 514/407 |
| 5,316,930 | 5/1994 | Loesch-Fries et al. | 435/468 |
| 5,354,684 | 10/1994 | Kerr et al. | 435/252.3 |
| 5,556,873 | 9/1996 | Huang et al. | 514/407 |
| 5,608,077 | 3/1997 | Hatton et al. | 536/365.1 |

FOREIGN PATENT DOCUMENTS 0 313 333    4/1989   (EP) .............................. C12N/15/00

OTHER PUBLICATIONS

Jaynes, J.M., "Use of Genes Encoding Novel Lytic Peptides and Proteins that Enhance Microbial Disease Resistance in Plants," *Acta. Horticulturae.* pp. 33–39 (1993).
Mullins et al., "Agrobacterium–Mediated Genetic Transformation of Grapevines: Transgenic Plants of *Vitis Rupestris* Scheele and Buds of *Vitis Vinifera,*" *Bio. Technology* 8:1041–1045 (1990).
Scorza et al, J. Amer. Soc. Hort. Sci., vol. 121, pp. 616–619, 1996.*
Sule et al, Phytopath., vol. 84, pp. 607–611, 1994.*
Tinland et al, Proc. Natl. Acad. Sci. USA, vol. 89, pp. 7442–7446, 1992.*
Barton et al., "Regeneration of Intact Tobacco Plants Containing Full Length Copies of Genetically Engineered T–DNA, and Transmission of T–DNA to R1 Progeny," *Cell* 32:1033–1043 (1983).
Belanger et al., "Genetic Analysis of Nonpathogenic *Agrobacterium tumefaciens* Mutants Arising in Crown Gall Tumors," *Journal of Bacteriology* 177:3752–3757 (1995).
Binns et al., "Inhibition of VirB–Mediated Transfer of Diverse Substrates from *Agrobacterium tumefaciens* by the IncQ Plasmid RSF1010," *Journal of Bacteriology* 177:4890–4899 (1995).
Citovsky et al., "Nuclear Localization of Agrobacterium VirE2 Protein in Plant Cells," *Science* 256:1802–1805 (1992).
Citovsky et al., "Nuclear Import of Agrobacterium VirD2 and VirE2 Proteins in Maize and Tobacco," *Proc. Natl. Acad. Sci. USA* 91:3210–3214 (1994).
Clare, "Agrobacterium in Plant Disease, Biological Disease Control and Plant Genetic Engineering," *Science Progress* 74:1–13 (1990).
Clare et al., "Characteristics of the Nopaline Catabolic Plasmid in Agrobacterium Strains K84 and K1026 Used for Biological Control of Crown Gall Disease," *Plasmid* 23:126–127 (1990).
Dhandayuthapani et al., "Oxidative Stress Response and its Role in Sensitivity to Isoniazid in Mycobacteria: Characterization and Inducibility of ahpC by Peroxides in *Mycobacterium Smegmatis* and Lack of Expression in *M. aurum* and *M. tuberculosis,*" *Journal of Bacteriology* 178:3641–3649 (1996).
Dombeck et al., "Functional Domains of *Agrobacterium tumefaciens* Single–Stranded DNA–Binding Protein VirE2," *Journal of Bacteriology* 179:1165–1173 (1997).
Gerard et al., "Physical Map of the Vitopine Ti Plasmid pTiS4," *Plasmid* 28:146–156 (1992).
Goddijn et al., "Overexpression of a Tryptophan Decarboxylase cDNA in *Catharanthus roseus* Crown Gall Calluses Results in Increased Tryptamine Levels but not in Increased Terpenoid Indole Alkaloid Production," *Transgenic Research* 4:315–323 (1995).
Guralnick et al., "Transport of DNA into the Nuclei of Xenopus Oocytes by a Modified VirE2 Protein of Agrobacterium," *The Plant Cell* 8:363–373 (1996).
Htay et al., "Biological Control of Crown Gall: Seed and Root Inoculation," *J. appl. Bact.* 37:525–530 (1974).
Huss et al., "Functional Analysis of a Complex Oncogene Arrangement in Biotype III *Agrobacterium tumefaciens* Strains," *Plant Molecular Biology* 14:173–186 (1990).
Kirpes et al., 1984 "Cost Analysis of Crown Gall Control on Grape Vines," Res. Bull. XB Washington State University Agricultural Research Center Pullman; Issue 0938.
Otten et al., "The Ti Plasmid from the Wide Host Range *Agrobacterium vitis* Strain Tm4: Map and Hornology with Other Ti Plasmids," *Plasmid* 29:154–159 (1993).

(List continued on next page.)

Primary Examiner—Elizabeth F. McElwain
Assistant Examiner—Ashwin D. Mehta
(74) Attorney, Agent, or Firm—Clark & Elbing LLP

(57) ABSTRACT

The invention relates to a transgenic grapevine or transgenic grapevine component transformed with a vir gene or an anti-pathogenic fragment thereof, wherein expression of the vir gene or the anti-pathogenic fragment thereof in the transgenic grapevine or transgenic grapevine component provides resistance to a plant bacterial pathogen (e.g., *Agrobacterium vitis*).

26 Claims, 2 Drawing Sheets

OTHER PUBLICATIONS

Otten et al., "*Agrobacterium vitis* Nopaline Ti Plasmid pTiAB4: Relationship to other Ti Plasmids and T–DNA Structure," *Mol. Gen. Genet* 245:493–505 (1994).

Sundberg et al., "VirE1 Protein Mediates Export of the Single–Stranded DNA–Binding Protein VirE2 from *Agrobacterium tumefaciens* into Plant Cells," *Journal of Bacteriology* 178:1207–1212 (1996).

Szegedi et al., "Further Evidence that the Vitopine–Type pTi's of *Agrobacterium vitis* Represent a Novel Group of Ti Plasmids," *Molecular Plant–Microbe Interactions* 9:139–143 (1996).

Tait et al., "Genetic Map of the Crown Gall Suppressive IncW Plasmid pSa," *Mol. Gen. Genet* 186:10–15 (1982).

Zupan et al., "Transfer of T–DNA from Agrobacterium to the Plant Cell," *Plant Physiol.* 107:1041–1047 (1995).

* cited by examiner

SEQUENCE LISTING

<160> NUMBER OF SEQ ID NOS: 2

<210> SEQ ID NO 1
<211> LENGTH: 29
<212> TYPE: DNA
<213> ORGANISM: Artificial Sequence

```
                                      -continued

<220> FEATURE:
<223> OTHER INFORMATION: Synthetic primer

<400> SEQUENCE: 1
tacttaccat ggatccgaag gccgaaggc                                              29

<210> SEQ ID NO 2
<211> LENGTH: 37
<212> TYPE: DNA
<213> ORGANISM: Artificial Sequence
<220> FEATURE:
<223> OTHER INFORMATION: Synthetic primer

<400> SEQUENCE: 2
tcttgaccat ggctatcgat tctcgccggc ggaactc                                     37
```

BACTERIAL RESISTANCE IN GRAPEVINE

CROSS REFERENCE TO RELATED APPLICATIONS

This application claims benefit from provisional application 60/062,246, filed on Oct. 17, 1997.

BACKGROUND OF THE INVENTION

This invention relates to disease resistance in plants.

Grapes are the most widely grown fruit crop in the world and are difficult to breed by conventional methods (Mullins et al., *BioTechnology* 8:1041–1045, 1990). There has been considerable effort targeted toward the production of transgenic grape cultivars. Recently, transformation of grape cultivars has been successful using embryogenic calli or suspension cultures for transformation. Transgenic plants have been recovered for rootstock cultivars Rupestris St. George (*Vitis rupestris*, Mullins et al., *BioTechnology* 8:1041–1045, 1990), Richter 110(*V. rupestris x V. berlandieri*, LeGall et al., *Plant Science* 102:161–170, 1994; Krastanova et al., *Plant Cell Reports* 14:550–554, 1995), 41B (*V. berlandieri x V. rupestris*, Mauro et al., *Plant Science* 112:97–106, 1995), as well as scion cultivars Chancellor (*Vitis spp.*, Kikkert et al., *Plant Cell Reports* 15:311–316, 1996), Thompson Seedless (*V. vinifera*, Scorza et al., *J. Amer. Soc. Hort. Sci.* 121:616–619, 1996), and Superior seedless (*V. vinifera*, Perl et al., *Plant Science* 104:193–200, 1996). Many of the genes introduced into such grape cultivars have been coat protein genes of grapevine viruses, including grapevine fanleaf virus (Mauro et al., 1995; Krastanova et al., *Plant Cell Reports* 14:550–554, 1995), grapevine chrome mosaic virus (LeGall et al., *Plant Science* 102:161–170, 1994), and tomato ringspot virus (Scorza et al., *J. Amer. Soc. Hort. Sci.* 121:616–619, 1996). Additionally, transformation with a gene encoding a lytic peptide, Shiva-1, has been reported (Scorza et al., *J. Amer. Soc. Hort. Sci.* 121:616–619, 1995). Use of these techniques and others provides the basis for engineering disease resistance in grapes; e.g., developing transgenic grape plants that are resistant to infestation by pests (e.g., insects and nematodes) and to attack by pathogenic microorganisms (e.g., fungi, bacteria, and viruses).

One microbial induced disease found in grapes is crown gall disease. It is caused by Agrobacterium spp., a soil-inhabiting, gram-negative bacterium. Persisting for long-periods of time in plant debris found in the soil, this bacterium has one of the widest host ranges of any plant pathogen. These bacteria induce galls or plant tumors on the roots, crowns, trunks, and canes of plants.

Agrobacterium causes crown gall by copying and transferring a segment of its tumor-inducing (Ti) plasmid, referred to as the transfer DNA (T-DNA), to the plant cell where it is integrated into the plant cell genome. Transfer of the T-DNA into the plant cell nucleus is dependent on the expression of various virulence (vir) genes that are also located on the Ti plasmid. One virulence protein, VirD2, is a site-specific endonuclease which, when assisted by the VirD1 protein, recognizes and nicks the 'bottom strand' of the left and right T-DNA border sequences (Stachel et al., *EMBO J.* 6:857–863, 1987). The VirD2-protein becomes covalently attached to the 5' end of the nicked strand (Ward and Barnes, *Science* 242:927–930, 1988). The single-stranded T-DNA (ssT-DNA) is then exported to the plant cell (Tinland et al., *Proc. Natl. Acad. Sci.* 91:8000–8004, 1994, Yusibov et al., *Proc. Natl. Acad. Sci.* 91:2994–2998, 1994).

A current hypothesis for the transport of T-DNA to the plant cell nucleus is that the ssT-DNA is coated by molecules of the VirE2 protein, which has been shown to bind ssT-DNA. Coated T-DNA, referred to as the T-complex, is thought to be exported to the plant cell via a pore formed by VirB proteins. T-complexes may be imported into the nucleus using a plant-protein pathway; involving the transport of proteins having nuclear localization signals to the nucleus. Both VirD2 and VirE2 are required for optimal transfer of T-DNA to the plant cell nucleus. The T-complex therefore travels from Agrobacterium into the plant cell where the T-DNA is integrated into the plant genome.

Agrobacterium's T-DNA encodes a number of enzymes involved in auxin and cytokinin biosynthetic pathways. Infected cells overproduce the plant hormones auxin and cytokinin, leading to rapid and uncontrolled cell division, and the formation of galls or plant tumors. Gall formation interferes with water and nutrient flow in the plant. Infected plants typically become unproductive and are more susceptible to adverse environmental conditions. The disease is especially destructive on fruit crops such as grapes.

Crown gall of grape is caused almost exclusively by *A. vitis* and to a lesser extent by *A. tumefaciens*. The bacterium infects the grapevine at wound sites in the trunk, and leads to the formation of galls. Bacteria survive in grapevine xylem, and are disseminated by infected propagating materials. Agrobacterium infections are particularly damaging to young vines during vineyard establishment; rapidly growing galls are capable of girdling young vines in a single season (Agrios, *Plant Pathology*, 3rd edition, Academic Press, 1998). Infected vines have reduced yield and productivity.

SUMMARY OF THE INVENTION

In general, the invention features a method for providing resistance to a bacterial pathogen in a plant (e.g., a grapevine such as Vitis). The method generally involves the steps of: (a) transforming plant cells with a virulence (vir) gene or an anti-pathogenic fragment thereof; (b) regenerating the plant cells to provide a differentiated plant; and (c) selecting a transformed plant which expresses the vir gene or the anti-pathogenic fragment thereof, wherein expression of the vir gene or the anti-pathogenic fragment thereof provides resistance to the plant bacterial pathogen. In general, the processing and transfer of T-DNA from bacterium to plant are mediated by gene products encoded by the vir region residing on the tumor-inducing (Ti) or root-inducing (Ri) plasmids of Agrobacterium. Exemplary vir genes useful in the invention include, without limitation, virE2 and virD2.

In preferred embodiments of the invention, the vir gene or anti-pathogenic fragment thereof is integrated into the genome of the plant. Preferably, the vir gene is virE2, virD2, or both; or is mutated (e.g., is an anti-pathogenic vir gene fragment such as one encoding a deletion of a Vir protein such as the virE2 deletion B, virE2 deletion C, or virE2 deletion E). vir sequences that mediate an increased resistance to crown gall disease are considered useful in the invention. As used herein, the term "fragment," as applied to sequences of a nucleic acid molecule, means at least 5 contiguous nucleotides, preferably at least 10 contiguous nucleotides, more preferably at least 20 to 30 contiguous nucleotides, and most preferably at least 40 to 80 or more contiguous nucleotides. Natural or synthetic fragments of a vir gene (e.g., virE2 or virD2) can be produced and, subsequently, integrated into any standard plant expression vector (e.g., those described herein) according to methods known to those skilled in the art. The ability of such vir gene fragments (e.g., a vir gene encoding deletion B, deletion C, deletion D, or deletion E of the virE2 gene) to confer resistance, when expressed in a plant, to a bacterial plant pathogen can be tested according to standard methods (e.g., those described herein). Fragments conferring resistance to a plant bacterial pathogen are referred to as "anti-pathogenic fragments."

In preferred embodiments, the plant is a grapevine or a grapevine component (e.g., a somatic embryo, scion, or a rootstock); the bacterial pathogen is *Agrobacterium vitis* or *Agrobacterium tumefaciens*; and resistance to *Agrobacterium vitis* or *Agrobacterium tumefaciens* reduces crown gall formation or growth of such bacteria on the infected plant. In yet other preferred embodiments, the vir gene (or an anti-pathogenic fragment thereof) is from a tumor-inducing (Ti) or root-inducing (Ri) plasmid of Agrobacterium (e.g., *Agrobacterium vitis, Agrobacterium tumefaciens, Agrobacterium rhizogenes*). Examples of such Ti plasmids, without limitation, include nopaline-, vitopine-, octopine-, octopine/cucumopine-, leucinopine/agropine-, succinamopine-, or agropine-type Ti plasmids. Such vir gene sequences or anti-pathogenic fragments are obtained according to standard methods known in the art The methods described herein are useful for providing disease resistance or tolerance or both on a variety of grapevines (e.g., Vitis spp., Vitis spp. hybrids, and all members of the subgenera Euvitis and Muscadinia) to bacterial pathogens (e.g., *Agrobacterium vitis* or *A. tumefaciens*), including scion and rootstock cultivars. Exemplary scion cultivars include, without limitation, those which are referred to as table or raisin grapes and those used in juice and wine production such as Cabernet Franc, Cabernet Sauvignon, Chardonnay (e.g., CH 01, CH 02, CH Dijon), Merlot, Pinot Noir (PN, PN Dijon), Semillon, White Riesling, Lambrusco, Thompson Seedless, Autumn Seedless, Niagrara Seedless, and Seval Blanc. Rootstock cultivars that are useful in the invention include, without limitation, *Vitis rupestris* Constantia, *Vitis rupestris* St. George, *Vitis california, Vitis girdiana, Vitis rotundifolia, Vitis rotundifolia* Carlos, Richter 110(*Vitis berlandieri x rupestris*; "110R"), 101–14 Millarder et de Grasset (*Vitis riparia x rupestris*; "101-14 Mgt"), Teleki 5C (*Vitis berlandieri x riparia*), Courderc 3309 (*Vitis riparia x rupestris*; "C3309"), Riparia Gloire de Montpellier (*Vitis riparia*), 5BB Teleki (selection Kober, *Vitis berlandieri x riparia*), SO$_4$ (*Vitis berlandieri x rupestris*), 41B Millardet (*Vitis vinifera x berlandieri*), Ramsey (*Vitis champinii*), K5140 (*Vitis champinii x Vitis riparia*), and 039-16 (*Vitis vinifera x Muscadinia*).

The invention also features scions, rootstocks, somatic or zygotic embryos, cells, or seeds that are produced from any of the transgenic grapevines or grapevine components described herein. For example, the invention features a transgenic plant transformed with a nucleic acid molecule which encodes a Vir protein or an anti-pathogenic fragment thereof, where the expression of the nucleic acid molecule provides resistance to a bacterial pathogen (e.g., *A. vitis* or *A. tumefaciens*). The invention also includes a grape cell which has been transformed with a nucleic acid molecule (e.g., a virE2 deletion B transgene construct which is positioned for expression by operably linking the transgene to a plant expression control region) that provides resistance to a bacterial pathogen. Such grape cells are then used to generate rootstocks, scions, somatic embryos, or seeds using methods that are known in the art (e.g., those described herein).

By "positioned for expression" is meant that the DNA molecule is positioned adjacent to a DNA sequence which directs transcription of the sequence.

By "expression control region" is meant any sequence sufficient to direct transcription. Included in the invention are promoter and enhancer elements that are sufficient to render promoter-dependent gene expression controllable for cell-, tissue-, or organ-specific gene expression, or elements that are inducible by external signals or agents (e.g., light-, pathogen-, wound-, stress- or hormone-inducible elements; or constitutive elements); such elements may be located in the 5' or 3' regions of the native gene or engineered into a transgene construct.

By "operably linked" is meant that a gene and a regulatory sequence(s) are connected in such a way to permit gene expression when the appropriate molecules (e.g., transcriptional activator proteins) are bound to the regulatory sequence(s).

By "plant cell" is meant any self-propagating cell bound by a semi-permeable membrane and containing a plastid. A plant cell, as used herein, is obtained from, without limitation, seeds, suspension cultures, embryos, meristematic regions, callus tissue, protoplasts, leaves, roots, shoots, somatic and zygotic embryos, as well as any part of a reproductive or vegetative tissue or organ.

By "plant component" is meant a part, segment, or organ obtained from an intact plant or plant cell. Exemplary plant components include, without limitation, somatic embryos, leaves, fruits, scions, and rootstocks.

By "transgenic" is meant any cell which includes a DNA sequence which is inserted by artifice into a cell and becomes part of the genome of the organism (integrated or extrachromosomal) which develops from that cell. As used herein, the transgenic organisms are generally transgenic grapevines or grapevine components and the DNA (e.g., a transgene) is inserted by artifice into the nuclear or plastidic compartments of the plant cell. Preferably, such transgenic grapevine or grapevine component express at least one vir nucleic acid sequence (e.g., a vir gene or an anti-pathogenic fragment thereof such as virE2 deletion B from *A. vitis* strain CG450). In other preferred embodiments, a transgenic plant may express more than one vir sequence or a combination of vir sequences (e.g., a vir nucleic acid sequence derived from different Ti plasmids such as the nopaline-, vitopine-, octopine-, octopine/cucumopine-, leucinopine/agropine-, succinamopine-, or agropine-type Ti or Ri plasmids).

By "transgene" is meant any piece of DNA which is inserted by artifice into a cell, and becomes part of the organism (integrated into the genome or maintained extrachromosomally) which develops from that cell. Such a transgene may include a gene which is partly or entirely heterologous (i.e., foreign) to the transgenic organism, or may represent a gene homologous to an endogenous gene of the organism.

By "resistance to a plant bacterial pathogen" is meant a greater level of resistance to a pathogen (e.g., *Agrobacterium vitis* or *A. tumefaciens*) in a transgenic grapevine (or grapevine component or cell, seed, or somatic embryo thereof) than the level of resistance relative to a control grapevine (e.g., a non-transgenic grapevine). In preferred embodiments, the level of resistance to a pathogen in a transgenic grapevine is at least 5 to 10% (and preferably 20%, 30%, or 40%) greater than the resistance of a control grapevine. In other preferred embodiments, the level of resistance to the pathogen is 50% greater, 60% greater, and more preferably even 75% or 90% greater than a control grapevine; with up to 100% resistance as compared to a control grapevine being most preferred. The level of resistance is measured using conventional methods. For example, the level of resistance to Agrobacterium may be determined by comparing physical features and characteristics (e.g., plant height and weight, or by comparing disease symptoms, e.g., delayed galling, reduced galling, or reduced deformity of canes) of transgenic grapevines or by comparing the population of a pathogen surviving on the plant (e.g., by measuring the systemic population of Agrobacterium on transgenic and control plants).

As is discussed above, it has been discovered that the expression of a vir nucleic acid sequence, virE2 deletion B, provides transgenic grapevines with resistance against crown gall disease caused by the bacterium, Agrobacterium. Accordingly, because there are no viable alternatives for controlling Agrobacterium on grapes, the invention provides a number of important advances and advantages for viticulturists. For example, by demonstrating that the sequence is effective against the development of crown gall disease, the invention facilitates an effective and economical means for protection against the disease. Such protection reduces or minimizes the need for traditional practices, e.g., chemical treatments, that are typically used by viticulturists for controlling the spread of Agrobacterium and providing protection against this disease-causing pathogen in vineyards. In addition, because grape plants expressing vir nucleic acid sequences or anti-pathogenic fragments are less vulnerable to Agrobacterium (e.g., *A. vitis* and *A. tumefaciens*) and thus crown gall disease, the invention further provides for increased production efficiency, as well as for improvements in quality, color, flavor, and yield of grapes. Furthermore, because the invention reduces the necessity for chemical protection against grapevine pathogens, it benefits the environment where the vineyards are planted.

Other features and advantages of the invention will be apparent from the following description of the preferred embodiments thereof, and from the claims.

DETAILED DESCRIPTION

The drawings will first be described.

DRAWINGS

OVERVIEW

Figure 1:
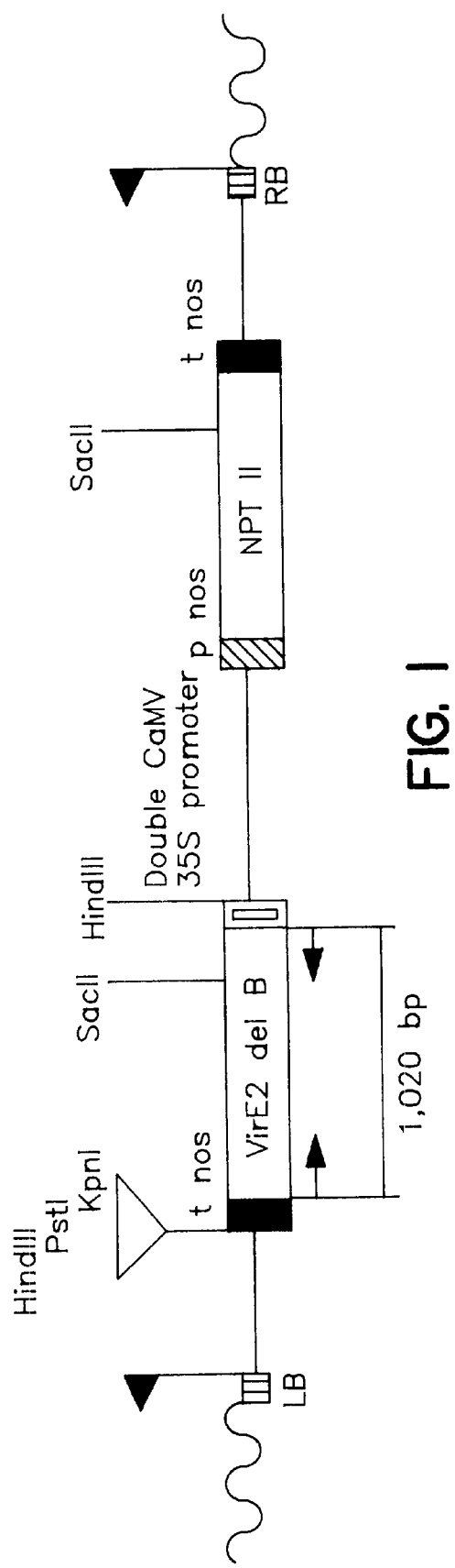
FIG. 1 is a schematic illustration showing the partial map of the T-DNA region containing the virE2 deletion B transgene under the control of the tandem CaMV 35S promoter.

A genetic study was conducted using *Agrobacterium tumefaciens* and *A. vitis* to identify Vir protein products (e.g., a deletion mutant of the virE2 gene) that are useful for increasing resistance to pathogenic infection of grape plants. Mutant virE2 deletion B transgene constructs (Citovsky et al., Science 256:1802–1806, 1992) were generated using *A. tumefaciens* strain C58 (which carries a nopaline-type Ti plasmid), *A. tumefaciens* strain A6 (which carries an octopine-type Ti plasmid), and *A. vitis* strain CG450 (which carries a vitopine Ti plasmid). The virE2 deletion B gene encodes a VirE2 protein that lacks 215 carboxy-terminal amino acids. This truncation deletes the single-stranded T-DNA (ssT-DNA) binding domain of the VirE2 protein. Grape rootstocks (e.g., Courderc 3309 (*Vitis riparia x rupestris*; "C3309"), 101–14 Millarder et de Grasset (*Vitis riparia x rupestris*; "101–14 Mgt"), and Richter 110 (*Vitis berlandieri x rupestris*; "110R")), as well as tobacco (e.g., *Nicotiana benthamiana*), were then transformed with a transgene which expressed the deletion B of the virE2 gene (FIG. 1). Transgenic plants expressing these transgene constructs were generated and disease resistance to crown gall disease was subsequently evaluated.

The following examples are now provided for the purpose of illustrating the invention, and should not be construed as limiting.

virE2 Deletion B Transgene Construction and Agrobacterium Strains virE2 deletion B gene constructs were generated as follows. The virE2 deletion B genes were mutant virE2 genes, lacking the region coding for a ssDNA binding motif (Citovsky et al., Science 256:1802–1805, 1992). These genes were obtained from *A. tuniefaciens* strain C58 and *A. tumefaciens* strain A6, which harbored nopaline- and octopine-type Ti plasmids, respectively. The virE2 deletion B gene was also generated from *A. vitis* strain CG450 which carries a vitopine-type Ti plasmid. The virE2 deletion B gene was amplified from *A. tumefaciens* strain C58 and from *A. vitis* strain CG450 DNA using the primer set 5' nop (5'-TACTTACCATGGATCCGAAGGCCGAAGGC; SEQ ID NO: 1), which is identical to the 5' coding region of the nopaline virE2 gene, and 3' nop (5'-TCTTGACCATGGCTATCGATTCTCGCCG-GCGGAACTC; SEQ ID NO: 2), hybridizing to nucleotide positions 1000–1020 of the same gene. The octopine-type virE2 deletion B mutant was amplified from *A. tumefaciens* strain A6 using the oligomer primers 5'oct (identical to the 5' region of the octopine-type virE2 gene) and 3'oct (complementary to nucleotide positions 927–951 from the translation initiation codon).

Polymerase chain reaction (PCR) amplification of the virE2 deletion B gene from different Ti plasmids was performed as follows. The virE2 deletion B gene was amplified using 0.5 µg each of oligomer primers according to the manufacturer's instructions (Perkin-Elmer Cetus). The PCR cycle was 1 minute at 92° C. (denaturing), 1 minute at 50° C. (annealing), and 2 minutes at 72° C. (polymerizing). Samples were directly loaded and separated on a 1.2% agarose gel. The separated virE2 deletion B fragments were extracted from the gel, ethanol precipitated, and dissolved in 20 µl of distilled $H_2O$. The gel-isolated mutant gene fragment was then digested with the restriction enzyme NcoI and directly cloned into NcoI digested plant expression vector pEPT8. The expression of virE2 coding sequences was thus controlled by a double CaMV 35S promoter fused to the 5'-untranslated leader sequence of alfalfa mosaic virus (AIMV) of the expression vector pEPT8. The expression cassette was excised from the construct with HindIII, and ligated into the plant transformation vector pBIN19 that had been cut with the same enzymes. The resulting transformation vectors, pBIN19-EPT8-virE2-C58 (FIG. 1), pBIN19-EPT8-virE2-A6, and pBIN19-EPT8-virE2-CG450 were transferred to *A. tumefaciens* strain C58sZ707 by electroporation according to standard methods.

Transformation of Grape and Tobacco with the virE2 Deletion B Transgene Constructs Embryogenic calli of C3309, 101-14 Mgt, and 110OR were transformed with the virE2 deletion B transgene constructs using an Agrobacterium co-cultivation method as follows.

Embryogenic calli capable of generating somatic embryos were developed from cultured anthers according to standard methods. Briefly, anthers of the rootstock clones C3309, 101-14 Mgt, and 110OR were used to initiate callus cultures by the method of Rajasekaran and Mullins (*J. Exp. Bot.* 30:399–407, 1979). Buds were harvested prior to anthesis from field-grown plants during the spring and early summer, removed from the clusters, and surface sterilized in 70% EtOH for 1 to 2 minutes. The buds were transferred to 1% sodium hypochlorite for 15 minutes, then rinsed 3 times in sterile double distilled water. Translucent yellow anthers were excised aseptically from flower buds. Anthers were isolated under sterile conditions and plated at a density of 40 or 50 anthers per petri dish on initiation medium. Anthers were cultured at 28° C. in the dark. Embryogenic calli developed within 30 days.

Overnight cultures of *A. tumefaciens* containing the virE2 deletion B transgene construct used for transformation were grown in LB medium at 28° C. in a shaking incubator. Bacteria were centrifuged for 5 minutes at 3000 rpm and resuspended in MS liquid medium (OD 0.4–0.5 at $A_{600}$ nm). Calli with globular or heart-shaped embryos were immersed in the bacterial suspension for 15 minutes, blotted dry, and transferred to HMG medium with acetosyringone (100 μM). Embryogenic callus tissue was cocultivated with the bacteria for 48 hours in the dark at 28° C. Then, the plant material was washed in MS liquid plus cefotaxime (300 μg/ml) and carbenicillin (200 μg/ml) 2–3 times. The material was transferred to HMG medium with the same antibiotics for 1–2 weeks. After 2 weeks, the embryogenic calli were transferred to HMG medium containing either 20 or 40 mg/L kanamycin and 300 mg/L cefotaxime, plus 200 mg/L carbenicillin to select transgenic embryos. After growth on selection medium for 3–4 months, embryos were transferred to HMG, MGC, or MSE without kanamycin. After approximately 4 months, all materials were transferred to medium without antibiotics. After development of hypocotyls, embryos were transferred to rooting medium without antibiotics.

Nontransformed calli were grown in the same medium with or without kanamycin as a control to verify the efficiency of the antibiotic selection and the regeneration ability of the material.

Transformation of Tobacco

Tobacco plants, *N. tabacum* and *N. benthamiana*, were transformed using a leaf disk transformation method (Horsch et al., *Science* 227:1229, 1985). The binary vector, pBIN19-EPT8-virE2-C58 and pBIN-EPT8-virE2-A6 were the same as used in the grape transformation (FIG. 1). Shoots were regenerated from the leaf pieces, excised from the original explant and allowed to root on MS media with kanamycin. Tobacco plants were allowed to self-fertilize and the R1 generation was used in the resistance assays.

Characterization of Transgenic Plants

Transgenic plants were recovered and verified by conventional NPTII-ELISA. Transgenic C3309, 101-14 Mgt, and 110R plants and lines of transgenic tobacco were recovered. Total DNA was extracted as described below from young leaves of selected plants and tested for the presence of the transgene by conventional polymerase chain reaction (PCR). The 1.020 kb PCR product corresponding to the virE2 deletion B transgene was observed in most transgenic plants.

Selected transgenic C3309 plants were further analyzed for gene copy number by Southern blot hybridization using the 1.0 kb virE2 deletion B gene as a probe. Both the susceptible and resistant plants had relatively few copies (1–4) of the transgene. The level of virE2 deletion B gene MRNA was examined by northern blot analysis as described below. Transgenic resistant plants were found to express higher levels of virE2 deletion B mRNA than susceptible plants.

For these above-mentioned assays, total DNA was isolated from plants as described by Krastanova et al. (*Plant Cell Reports* 14:550–554, 1995). PCR reactions were performed on total plant genomic DNA as described above, using an annealing temperature of 45° C. rather than 50° C. For Southern blot hybridization, 20 μg of DNA was digested with HindIII, PstI, and KpnI. Total genomic DNA was run on 1% agarose TBE gels and blotted to a Nytran N filter (Schleicher and Schuell, Keene, NH) according to manufacturer's instructions. The blot was dried in an 80° C. oven for one hour, then prehybridized and hybridized as described Sambrook et al. (*Molecular Cloning: A Laboratory Manual*, Cold Spring Harbor Laboratory Press, N.Y. 1989). The $^{32}P$ dCTP-labeled probe was constructed using the RadPrime DNA labeling system from Gibco BRL (Gaithersburg, Md.). RNA was extracted from transgenic plants by the same method as DNA extraction, total nucleic acid was precipitated overnight at −20° C. with 2M LiCl to select total RNA. RNA (20 μg) was run on denaturing formaldehyde gels as described by Sambrook et al. (supra), and blotted to Nytran-N, and prehybridized and hybridized using the same probe as for the Southern blots.

Disease Resistance

Resistance of transgenic lines of grape plants to crown gall disease was assayed as follows. Grape stem internodes were inoculated as described by Pu and Goodman (*Physiological and Molecular Plant Pathology* 41:241–254, 1992). The inoculum used in these experiments was either *A. tumefaciens* strain C58 or *A. tumefaciens* strain A6. Bacteria were grown at 28° C. for 48 hours on PDA medium, with antibiotics if appropriate. For inoculation, the bacteria were resuspended in sterile distilled $H_2O$ ($A_{600nm}$=0.1), which is approximately $1 \times 10^8$ cfu/ml for C58. Five μL of the inoculum or a dilution thereof was applied to the cut grape internodes, and the plants were observed for tumor formation at 7, 14, and 21 days post inoculation (dpi).

Nontransgenic controls inoculated with *A. tumefaciens* strains C58 or A6 consistently exhibited tumorigenesis. On susceptible plants, gall formation was occasionally seen at 7 dpi, but it generally appeared at about 10 dpi, and were easily observed by 14 dpi. Primary transformants were assayed and some of the primary transformants were found to inhibit gall formation. Some of the inoculated shoots did become tumorigenic. Plants were scored as resistant if galls were suppressed by 50% or more as compared to those on nontransformed shoots.

Figure 2:
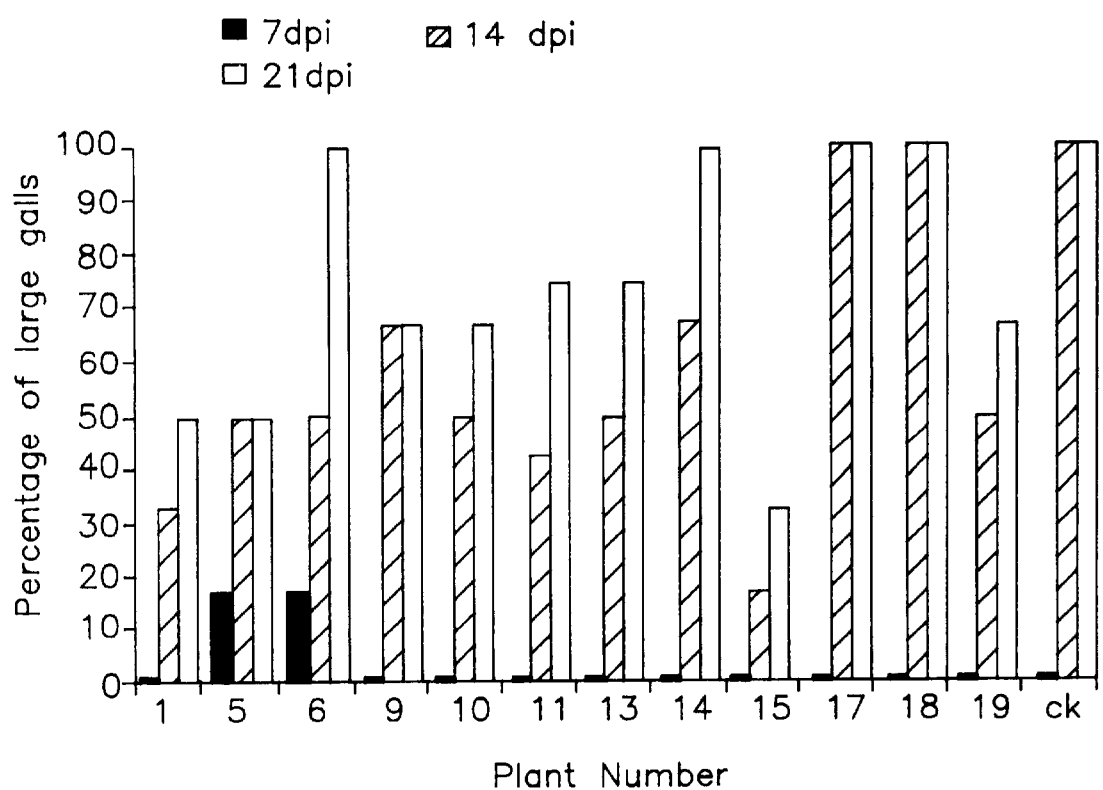
FIG. 2 is a bar graph showing that transformation of 101-Mgt with the virE2 deletion B gene generated from *Agrobacterium tumefaciens* strain A6 resulted in several transgenic lines having resistance when compared to control plants.

Lines of C3309, 101-Mgt, and 110R having resistance to crown gall have been generated. Exemplary results showing the resistance to crown gall formation of transgenic 101–14 Mgt (expressing the virE2 deletion B transgene which was generated from *A. tumefaciens* strain A6) after inoculation with *A. lumefaciens* strain A6 are presented in FIG. 2.

Furthermore, grape rootstock C3309 which expressed the virE2 deletion B transgene from *A. turnefaciens* strain C58 showed that about 45% of these plants had significant resistance to crown gall disease (Table 1, below).

TABLE 1

Evaluation of transgenic lines of grape rootstock C3309 expressing the virE2 deletion B transgene for resistance to crown gall by inoculation with A. tumefaciens strain C58

| Line No. | Plant No. | Resistance to Crown Gall |
| --- | --- | --- |
| 1 | 223, 224, 225, 228, 243 | susceptible |
| 2 | 240 | resistant |
| 3 | 218, 227 | susceptible |
| 3 | 169, 222 | resistant |
| 4 | 239 | susceptible |
| 5 | 245 | resistant |
| 6 | 234, 241 | susceptible |
| 11 | 235 | susceptible |
| 15 | 226 | resistant |
| 16 | 171, 220 | resistant |

Fifteen to twenty shoot sections from each plant were inoculated in vitro with a bacterial suspension of A. tumefaciens strain C58 (about $10^7$ cfu/ml). A plant was considered resistant if fewer than forty percent of the shoot inoculations developed galls six days after inoculation. One hundred percent of shoots from nontransgenic control plants developed galls.

Tobacco resistance to crown gall disease was assayed as follows. Transgenic tobacco plants were grown to a size of 6 cm. These plants were then inoculated with 10 μl of an overnight culture suspension of Agrobacterium strains CG49 or K306. Plants were checked for tumor formation 2–3 weeks after inoculation.

Lines of tobacco expressing the virE2 deletion B genes generated from A. tumefaciens strain C58 (carrying a nopaline-type Ti plasmid) and from A. tumefaciens strain A6 (carrying an octopine-type Ti plasmid) were also evaluated for crown gall disease resistance. These plants were inoculated with A. vitis strains CG49 (carrying a nopaline-type Ti plasmid) or A. vitis strain K306 (carrying an octopine-type Ti plasmid). Exemplary results of these experiments are shown in Table 2 (below).

TABLE 2

Exemplary resistance data for transgenic N. benthamiana expressing the virE2 deletion B transgene from A. tumefaciens strain C58 (carrying a nopaline-type Ti plasmid) and A. tumefaciens strain A6 (carrying an octopine-type Ti plasmid) inoculated with A. vitis strains CG49 (carrying a nopaline-type Ti plasmid) and A. vitis strain K306 (carrying an octopine-type Ti plasmid).

| Plant | virE2 expression | CG49 | CG49-1 | K306 | K306-1 | Susceptibility |
| --- | --- | --- | --- | --- | --- | --- |
| 1 | Oct,++++ | 1.0 | 0 | 0.25 | 0.25 | resistant |
| 2 | Oct,++ | 0.25 | 0 | 0.25 | 0.25 | resistant |
| 3 | Oct,+ | 2.5 | 2.5 | 1.0 | 1.0 | susceptible |
| 6 | Oct,++++ | 1.0 | 0.5 | 0.5 | 0.5 | resistant |
| 10 | Oct,+++ | 2.0 | 2.0 | 2.0 | 0.75 | susceptible |
| 11 | Oct,+++ | 2.0 | 0.5 | 0.75 | 0.25 | resistant to octopine type plasmid |
| 30 | Nop,+ | 0.75 | .75 | 1.0 | 0.5 | resistant |
| 31 | Nop,+++ | 2.5 | 2.5 | 3.0 | 3.0 | susceptible |
| 32 | Nop,++++ | 2.5 | 2.0 | 3.0 | 3.0 | susceptible |
| 34 | Nop,+ | 0 | 0.5 | 0.5 | 0.25 | resistant | virE2 expression was determined by northern blots and number of +'s indicates the strength of the signal. Plants were inoculated with a pathogen concentration of about $10^7$ cfu/ml and about $10^6$ cfu/ml. 0 = no gall or swelling at inoculation site. 0.5 = definite small gall at inoculation site; and 3 = very large gall at inoculation site. All nontransgenic control plants developed galls with ratings of 2–3.

Tobacco lines expressing the octopine virE2 deletion B transgene from A. tuinefaciens strain A6 or the nopaline virE2 deletion B transgene from A. tumefaciens strain C58 showed about a 50% reduction in crown gall disease when inoculated with A. vitis strain CG49 or A. vitis strain K306 (Table 2, supra).

Isolation of Vir Genes or Anti-Pathogenic Fragments Thereof

Any Ri or Ti plasmid (e.g., nopaline-, vitopine-, octopine-, octopine/cucumopine-, leucinopine/agropine-, succinamopine-, or agropine-type Ti plasmids) can serve as the nucleic acid source for the molecular cloning of a vir gene or an anti-pathogenic fragment thereof. For example, isolation of a vir gene (e.g., virE2 or virD2) involves the isolation of those DNA sequences which encode a protein exhibiting vir-associated structures, properties, or activities. Based on the nucleotide and amino acid sequences described for virE2 (see, e.g., GenBank Accession Nos. 2773266, 138480, 138481, 95134, 77949, 737146, 39124, 154801, and 154727) and virD2 (see, e.g., GenBank Accession Nos. 138464, 138463, 138465, 95129, 95128, 77931, 95077, 737141, 39000, 154829, and 154796), the isolation of vir coding sequences is made possible using standard strategies and techniques that are well known in the art.

In one particular example, the vir sequences described herein may be used, together with conventional nucleic acid hybridization screening methods. Such hybridization techniques and screening procedures are well known to those skilled in the art and are described, e.g., in Benton and Davis, Science 196: 180, 1977; Grunstein and Hogness, Proc. Natl. Acad. Sci., USA 72: 3961, 1975; Ausubel et al., Current Protocols in Molecular Biology, Wiley Interscience, New York; Berger and Kimmel, Guide to Molecular Cloning Techniques, 1987, Academic Press, New York; and Sambrook et al., Molecular Cloning: A Laboratory Manual, Cold Spring Harbor Laboratory Press, New York, 1989. In one particular example, all or part of the virE2 or virD2 nucleotide sequence (described by Citovsky, infra) may be used as a probe to screen a recombinant Ti plasmid DNA library for genes having sequence identity to the virE2 or virD2 genes. Hybridizing sequences are detected by plaque or colony hybridization according to standard methods, e.g. those described below.

Alternatively, using all or a portion of the amino acid sequence of a vir gene and the genetic code one may readily design vir-specific oligonucleotide probes, including vir degenerate oligonucleotide probes (i.e., a mixture of all possible coding sequences for a given amino acid sequence). These oligonucleotides may be based upon the sequence of either DNA strand and any appropriate portion of the vir sequence. General methods for designing and preparing such probes are provided, e.g., in Ausubel et al., 1996, Current Protocols in Molecular Biology, Wiley Interscience, New York, and Berger and Kimmel, Guide to Molecular Cloning Techniques, 1987, Academic Press, New York. These oligonucleotides are useful for vir gene isolation, either through their use as probes capable of hybridizing to vir complementary sequences or as primers for various amplification techniques, e.g., polymerase chain reaction (PCR) cloning strategies (e.g., those methods described herein). If desired, a combination of different oligonucleotide probes may be used for the screening of a recombinant DNA library. The oligonucleotides may be detectably-labeled using methods known in the art and used to probe filter replicates from a recombinant DNA library. Recombinant DNA libraries are prepared according to methods well known in the art, e.g., as described in Ausubel et al. (supra), or they may be obtained from commercial sources. Once a vir nucleotide sequence is identified, it is cloned and manipulated according to standard methods and used for the construction of plant expression vectors as described herein.

Construction of Plant Transgenes

In addition to transforming grape plants with a virE2 deletion B gene transgene construct, resistance to Agrobacterium infection can also be achieved by transforming such plants with the wild type virE2 gene or other virE2 mutant genes, e.g., deletion C (reducing polypeptide ssT-DNA and NSE1 binding activity, for example, by deletion of amino acids 228–244 of virE2 gene) or deletion D (reducing polypeptide ssT-DNA and NSE2 binding activity). One example of a virE2 deletion C mutation involves the production of transgene which encodes a VirE2 protein lacking amino acids 228–244 (Citovsky et al., *Science* 256:1802–1806, 1992). An example of a virE2 deletion D mutation involves the production of a transgene encoding a VirE2 protein lacking amino acids 296–310 (Citovsky et al., supra) Grape plants can also be transformed with virD2 wild type or virD2 mutant genes to confer resistance to Agrobacterium tumorigenicity. Mutations in the virD2 gene will also reduce nuclear transport of Agrobacterium ssT-DNA (e.g., mutations that inhibit the importation of the T-DNA strand into the plant nucleus, that enhance the activity of the nuclear localization signal, or that prevent binding of the VirD2 protein to the T-strand).

When the DNA sequences encoding the desired wild type or mutant vir gene is obtained, the sequences are inserted into a suitable plant transformation vector for transformation of the grape plant. A number of vectors suitable for stable or extrachromosomal transfection of plant cells or for the establishment of transgenic plants are available to the public; such vectors are described in Pouwels et al. (supra), Weissbach and Weissbach (supra), and Gelvin et al. (supra). Methods for constructing such cell lines are described in, e.g., Weissbach and Weissbach (supra), and Gelvin et al. (supra). Example of vectors useful for the expression of transgenes in grapevine are also described in Scorza et al. (*Plant Cell Reports* 14:589–592, 1995), Baribault et al. (*J. Expt. Bot.* 41:1045–1049, 1990), Mullins et al. (*BioTechnology* 8:1041–1045, 1990), Nakano et al. (*J. Expt. Bot.* 45:649–656, 1994), Kikkert et al. (*Plant Cell Reports* 15:311–316, 1995), Krastanova et al. (*Plant Cell Reports* 1:550–554, 1995), Scorza et al. (*Plant Cell Reports* 14:589–592, 1994), Scorza et al. (*J. Amer. Soc. Hort. Sci.* 121:616–619, 1996), Martinelli et al. (*Theor Appl Genet.* 88:621–628, 1994), and Legall et al. (*Plant Sci.* 102:161–170, 1994).

Typically, plant expression vectors include (1) a cloned gene (e.g., a wild type or mutated vir gene) under the transcriptional control of 5' and 3' expression control sequences and (2) a dominant selectable marker. Such plant expression vectors may also contain, if desired, a promoter regulatory region (e.g., one conferring inducible or constitutive, pathogen- or wound-induced, environmentally- or developmentally-regulated, or cell- or tissue-specific expression), a transcription initiation start site, a ribosome binding site, an RNA processing signal, a transcription termination site, and/or a polyadenylation signal.

In its component parts, a DNA sequence encoding a wild type or mutated vir gene is combined in a DNA construct having a transcription initiation control region capable of promoting transcription in a host grapevine cell. In general, the constructs will generally include regulatory regions functional in plants which provide for modified production of a wild type or mutated Vir protein as discussed herein. The sequence, mutated sequence, or fragment thereof will be joined at its 5' end to a transcription initiation regulatory region, e.g., such as a sequence naturally found in the 5' upstream region of a plant structural gene. Numerous transcription initiation regions are available which provide for constitutive or inducible regulation.

For applications where developmental, cell, tissue, hormonal, or environmental expression is desired, appropriate 5' upstream non-coding regions are obtained from other genes, e.g., from genes regulated during meristem development, seed development, embryo development, leaf development, stem development, or tendril development.

Regulatory transcript termination regions may also be provided in DNA constructs of this invention as well. Transcript termination regions may be provided by any convenient transcription termination region derived from a conventional gene sources (e.g., the NOS or 35S CaMV terminators). The transcript termination region will contain preferably at least 1–3 kb of sequence 3' to the structural gene from which the termination region is derived. Plant expression constructs having a wild type or mutated vir gene as the DNA sequence of interest for expression may be employed with a wide variety of grapevines. Such genetically-engineered plants are useful for a variety of industrial and agricultural applications. Importantly, this invention is applicable to all grapevines or grapevine components, and will be readily applicable to any new or improved transformation or regeneration methods of grape.

The expression constructs include at least one promoter operably linked to at least one wild type or mutated vir gene sequence. An example of a useful plant promoter according to the invention is a caulimovirus promoter, e.g., a cauliflower mosaic virus (CaMV) promoter. These promoters confer high levels of expression in most plant tissues, and the activity of these promoters is not dependent on virally encoded proteins. CaMV is a source for both the 35S and 19S promoters. In most tissues of transgenic plants, the CaMV 35S promoter is a strong promoter (see, e.g., Odell et al., *Nature* 313:810, 1985). The CaMV promoter is also highly active in monocots (see, e.g., Dekeyser et al., *Plant Cell* 2:591, 1990; Terada and Shimamoto, *Mol. Gen. Genet.* 220:389, 1990). Moreover, activity of this promoter can be further increased (i.e., between 2–10 fold) by duplication of the CaMV 35S promoter (see e.g., Kay et al., *Science* 236:1299, 1987; Ow et al., *Proc. Natl. Acad. Sci., U.S.A.* 84:4870, 1987; and Fang et al., *Plant Cell* 1:141, 1989, and McPherson and Kay, U.S. Pat. No. 5,378,142).

Other useful plant promoters include, without limitation, the nopaline synthase (NOS) promoter (An et al., *Plant Physiol.* 88:547, 1988), the octopine synthase promoter (Fromm et al., *Plant Cell* 1:977, 1989), the rice actin promoter (Wu and McElroy, WO91/09948), the cyclase promoter (Chappell et al., WO96/36697), and the cassava vein mosaic virus promoter (Verdaguer et al., *Plant Mol. Biol.* 31:1129–1139, 1996). Still other exemplary promoters useful in the invention include, without limitation, commelina yellow mottle virus promoter, sugar cane badna virus promoter, rice tungro bacilliform virus promoter, maize streak virus element, and wheat dwarf virus promoter.

For certain applications, it may be desirable to produce the wild type or mutated vir sequence in an appropriate tissue, at an appropriate level, or at an appropriate developmental time. For this purpose, there are an assortment of gene promoters, each with its own distinct characteristics embodied in its regulatory sequences, shown to be regulated in response to inducible signals such as the environment, hormones, and/or developmental cues. These include, without limitation, gene promoters that are responsible for heat-regulated gene expression (see, e.g., Callis et al., *Plant Physiol.* 88:965, 1988; Takahashi and Komeda, *Mol. Gen. Genet.* 219:365, 1989; and Takahashi et al. *Plant J.* 2:751, 1992), light-regulated gene expression (e.g., the pea rbcS-3A described by Kuhlemeier et al., *Plant Cell* 1:471, 1989; the maize rbcS promoter described by Schäffner and Sheen, *Plant Cell* 3:997, 1991; the chlorophyll a/b-binding protein gene found in pea described by Simpson et al., *EMBO J.* 4:2723, 1985; the Arabssu promoter; or the rice rbs promoter), hormone-regulated gene expression (e.g., the abscisic acid (ABA) responsive sequences from the Em gene of wheat described by Marcotte et al., *Plant Cell* 1:969, 1989; the ABA-inducible HVA1 and HVA22, and rd29A promoters described for barley and Arabidopsis by Straub et al., *Plant Cell* 6:617, 1994 and Shen et al., *Plant Cell* 7:295, 1995; and wound-induced gene expression (e.g., of wunI described by Siebertz et al., *Plant Cell* 1:961, 1989), organ-specific gene expression (e.g., of the tuber-specific storage protein gene described by Roshal et al., *EMBO J.* 6:1155, 1987; the 23-kDa zein gene from maize described by Schernthaner et al., *EMBO J.* 7:1249, 1988; or the French bean β-phaseolin gene described by Bustos et al., *Plant Cell* 1:839, 1989), or pathogen-inducible promoters (e.g., PR-1, prp-1, or β-1,3 glucanase promoters, the fungal-inducible wirla promoter of wheat, and the nematode-inducible promoters, TobRB7-5A and Hmg-1, of tobacco and parsley, respectively).

Plant expression vectors may also optionally include RNA processing signals, e.g, introns, which have been shown to be important for efficient RNA synthesis and accumulation (Callis et al., *Genes and Dev.* 1:1183, 1987). The location of the RNA splice sequences can dramatically influence the level of transgene expression in plants. In view of this fact, an intron may be positioned upstream or downstream of a vir gene sequence (or fragment thereof) in the transgene to modulate levels of gene expression.

In addition to the aforementioned 5' regulatory control sequences, the expression vectors may also include regulatory control regions which are generally present in the 3' regions of plant genes (Thornburg et al., *Proc. Natl. Acad. Sci. U.S.A.* 84:744, 1987; An et al., *Plant Cell* 1:115, 1989). For example, the 3' terminator region may be included in the expression vector to increase stability of the mRNA. One such terminator region may be derived from the PI-II terminator region of potato. In addition, other commonly used terminators are derived from the octopine or nopaline synthase signals.

The plant expression vector also typically contains a dominant selectable marker gene used to identify those cells that have become transformed. Useful selectable genes for plant systems include genes encoding antibiotic resistance genes, e.g., those encoding resistance to hygromycin, kanamycin, bleomycin, G418, streptomycin, or spectinomycin. Genes required for photosynthesis may also be used as selectable markers in photosynthetic-deficient strains. Finally, genes encoding herbicide resistance may be used as selectable markers; useful herbicide resistance genes include the bar gene encoding the enzyme phosphinothricin acetyltransferase and conferring resistance to the broad spectrum herbicide BASTA® (Hoechst AG, Frankfurt, Germany).

In addition, if desired, the plant expression construct may contain a modified or fully-synthetic translatable vir gene sequence (or fragment thereof) which has been changed to enhance the performance of the gene in plants.

It should be readily apparent to one skilled in the art of molecular biology, especially in the field of plant molecular biology, that the level of gene expression is dependent, not only on the combination of promoters, RNA processing signals, and terminator elements, but also on how these elements are used to increase the levels of selectable marker gene expression.

Grapevine Transformation and Regeneration

Upon construction of the plant expression vector, several standard methods are available for introduction of the vector into a plant host, thereby generating a transgenic plant. These methods include (1) Agrobacterium-mediated transformation (*A. turnefaciens* or *A. rhizogenes*) (see, e.g., Lichtenstein and Fuller In: *Genetic Engineering*, vol 6, PWJ Rigby, ed, London, Academic Press, 1987; and Lichtenstein, C. P., and Draper, J,. In: *DNA Cloning*, Vol II, D. M. Glover, ed, Oxford, IRI Press, 1985)), (2) the particle delivery system (see, e.g., Gordon-Kamm et al., *Plant Cell* 2:603 (1990); or BioRad Teclnical Bulletin 1687, supra), (3) microinjection protocols (see, e.g., Green et al., supra), (4) polyethylene glycol (PEG) procedures (see, e.g., Draper et al., *Plant Cell Physiol.* 23:451, 1982; or e.g., Zhang and Wu, Theor. *Appl. Genet.* 76:835, 1988), (5) liposome-mediated DNA uptake (see, e.g., Freeman et al., *Plant Cell Physiol.* 25:1353, 1984), (6) electroporation protocols (see, e.g., Gelvin et al., supra; Dekeyser et al., supra; Fromm et al., *Nature* 319:791, 1986; Sheen *Plant Cell* 2:1027, 1990; or Jang and Sheen *Plant Cell* 6:1665, 1994), and (7) the vortexing method (see, e.g., Kindle supra). The method of transformation is not critical to the invention. Any method which provides for efficient transformation may be employed. Some exemplary methods for transforming grapes are found in Scorza et al. (*Plant Cell Reports* 14:589–592, 1995), Baribault et al. (*J. Expt. Bot.* 41:1045–1049, 1990), Mullins et al. (*BioTechnology* 8:1041–1045, 1990), Nakano et al. (*J. Expt. Bot.* 45:649–656, 1994), Kikkert et al. (*Plant Cell Reports* 15:311–316, 1996), Krastanova et al. (*Plant Cell Reports* 1:550–554, 1995), Scorza et al. (*Plant Cell Reports* 14:589–592, 1994), Scorza et al.(*J. Amer. Soc. Hort. Sci.* 121:616–619, 1996), Martinelli et al. (*Theor Appl Genet.* 88:621–628, 1994), and Legall et al. (*Plant Sci.* 102:161–170, 1994). As newer methods are available to transform grapes they may be directly applied.

Suitable plants for use in the practice of the invention include, but are not limited to, grapevines (e.g., Vitis spp., Vitis spp. hybrids, and all members of the subgenera Euvitis and Muscadinia), including scion or rootstock cultivars. Exemplary scion cultivars include, without limitation, those which are referred to as table or raisin grapes and those used in wine production such as Cabernet Franc, Cabernet Sauvignon, Chardonnay (e.g., CH 01, CH 02, CH Dijon), Merlot, Pinot Noir (PN, PN Dijon), Semillon, White Riesling, Lambrusco, Thompson Seedless, Autumn Seedless, Niagrara Seedless, and Seval Blanc. Other scion cultivars which can be used include those commonly referred to as Table or Raisin Grapes, such as Alden, Almeria, Anab-E-Shahi, Autumn Black, Beauty Seedless, Black Corinth, Black Damascus, Black Malvoisie, Black Prince, Blackrose, Bronx Seedless, Burgrave, Calmeria, Campbell Early, Canner, Cardinal, Catawba, Christmas, Concord, Dattier, Delight, Diamond, Dizmar, Duchess, Early Muscat, Emerald Seedless, Emperor, Exotic, Ferdinand de Lesseps, Fiesta, Flame seedless, Flame Tokay, Gasconade, Gold, Himrod, Hunisa, Hussiene, Isabella, Italia, July Muscat, Khandahar, Katta, Kourgane, Kishmishi, Loose Perlette, Malaga, Monukka, Muscat of Alexandria, Muscat Flame, Muscat Hamburg, New York Muscat, Niabell, Niagara, Olivette blanche, Ontario, Pierce, Queen, Red Malaga, Ribier, Rish Baba, Romulus, Ruby Seedless, Schuyler, Seneca, Suavis (IP 365), Thompson seedless, and Thomuscat. They also include those used in wine production, such as Aleatico, Alicante Bouschet, Aligote, Alvarelhao, Aramon, Baco blanc (22A), Burger, Cabernet franc, Cabernet, Sauvignon, Calzin, Carignane, Charbono, Chardonnay, Chasselas dore, Chenin blanc, Clairette blanche, Early Burgundy, Emerald Riesling, Feher Szagos, Femao Pires, Flora, French Colombard, Fresia, Furmint, Gamay, Gewurztraminer, Grand noir, Gray Riesling, Green Hungarian, Green Veltliner, Grenache, Grillo, Helena, Inzolia, Lagrein, Lambrusco de Salamino, Malbec, Malvasia bianca, Mataro, Melon, Merlot, Meunier, Mission, Montua de Pilas, Muscadelle du Bordelais, Muscat blanc, Muscat Ottonel, Muscat Saint-Vallier, Nebbiolo, Nebbiolo fino, Nebbiolo Lampia, Orange Muscat, Palomino, Pedro Ximenes, Petit Bouschet, Petite Sirah, Peverella, Pinot noir, Pinot Saint-George, Primitivo di Gioa, Red Veltliner, Refosco, Rkatsiteli, Royalty, Rubired, Ruby Cabernet, Saint-Emilion, Saint Macaire, Salvador, Sangiovese, Sauvignon blanc, Sauvignon gris, Sauvignon vert, Scarlet, Seibel 5279, Seibel 9110, Seibel 13053, Semillon, Servant, Shiraz, Souzao, Sultana Crimson, Sylvaner, Tannat, Teroldico, Tinta Madeira, Tinto cao, Touriga, Traminer, Trebbiano Toscano, Trousseau, Valdepenas, Viognier, Walschriesling, White Riesling, and Zinfandel.

Rootstock cultivars that are useful in the invention include, without limitation, *Vitis rupestris* Constantia, *Vitis rupestris* St. George, *Vitis california, Vitis girdiana, Vitis rotundifolia, Vitis rotundifolia* Carlos, Richter 110 (*Vitis berlandieri x rupestris*), 101–14 Millarder et de Grasset (*Vitis riparia x rupestris*), Teleki 5C (*Vitis berlandieri x riparia*), 3309 Courderc (*Vitis riparia x rupestris*), Riparia Gloire de Montpellier (*Vitis riparia*), 5BB Teleki (selection Kober, *Vitis berlandieri x riparia*), SO$_4$ (*Vitis berlandieri x rupestris*), 41B Millardet (*Vitis vinifera x berlandieri*), and 039–16 (*Vitis vinifera x Muscadinia*). Additional rootstock cultivars which can be used include Couderc 1202, Couderc 1613, Couderc 1616, Dog Ridge, Foex 33EM, Freedom, Ganzin 1 (AxR #1), Harmony, Kober 5BB, LN33, Millardet & de Grasset 41B, Millardet & de Grasset 420A, Millardet & de Grasset 101–14, Oppenheim 4 (SO4), Paulsen 775, Paulsen 1045, Paulsen 1103, Richter 99, Richter 110, Riparia Gloire, Ruggeri 225, Saint-George, Salt Creek, Teleki 5A, *Vitis rupestris* Constantia, *Vitis california*, and *Vitis girdiana*.

In general, transfer and expression of transgenes in plant cells are now routine practices to those skilled in the art, and have become major tools to carry out gene expression studies in plants and to produce improved plant varieties of agricultural or commercial interest.

Plant cells transformed with a plant expression vector can be regenerated, e.g., from single cells, callus tissue, or leaf discs according to standard plant tissue culture techniques. It is well known in the art that various cells, tissues, and organs from almost any plant can be successfully cultured to regenerate an entire plant; such techniques are described, e.g., in Vasil supra; Green et al., supra; Weissbach and Weissbach, supra; and Gelvin et al., supra. Exemplary methods for regenerating grape plants from transformed material are found in found in Scorza et al. (*Plant Cell Reports* 14:589–592, 1995), Baribault et al. (*J. Expt. Bot.* 41:1045–1049, 1990), Mullins et al. (*BioTechnology* 8:1041–1045, 1990), Nakano et al. (*J. Expt. Bot.* 45:649–656, 1994), Kikkert et al. (*Plant Cell Reports* 15:311–316, 1996), Krastanova et al. (*Plant Cell Reports* 1:550–554, 1995), Scorza et al. (*Plant Cell Reports* 14:589–592, 1994), Scorza et al.(*J. Amer. Soc. Hort. Sci.* 121:616–619, 1996), Martinelli et al. (*Theor Appl Genet.* 88:621–628, 1994), and Legall et al. (*Plant Sci.* 102:161–170, 1994).

In one particular example, a cloned vir transgene constrict (e.g., virE2, virD2, virE2 deletion B, virE2 deletion C or virE2 deletion E mutation based on the virE2 coding sequences of a nopaline-, vitopine-, octopine-, octopine/cucumopine-, leucinopine/agropine-, succinamopine-, or agropine-type Ti plasmids or based on the such coding sequences which residing on Ri plasmids) under the control of the 35S CaMV promoter and the nopaline synthase terminator and carrying a selectable marker (e.g., kanamycin resistance) is transformed into Agrobacterium. Transformation of grapevine with vector-containing Agrobacterium is carried out as described by Scorza et al. (*J. Amer. Soc. Hort. Sci.* 121:616–619, 1996). Putative transformants are selected after a few weeks on plant tissue culture media containing kanamycin. Kanamycin-resistant plant material is then placed on plant tissue culture media without hormones for root initiation.

Transgenic plants expressing the selectable marker are then screened for transmission of the transgene DNA by standard detection techniques as described above. Each positive transgenic plant and its transgenic progeny are unique in comparison to other transgenic plants established with the same transgene. Integration of the transgene DNA into the plant genomic DNA is in most cases random, and the site of integration can profoundly affect the levels and the tissue and developmental patterns of transgene expression. Consequently, a number of transgenic lines are usually screened for each transgene to identify and select plants with the most appropriate expression profiles.

Transgenic lines are evaluated for levels of transgene expression. Expression at the RNA level is determined initially to identify and quantitate expression-positive plants. Standard techniques for RNA analysis are employed and include PCR amplification assays using oligonucleotide primers designed to amplify only transgene RNA templates and solution hybridization assays using transgene-specific probes (see, e.g., Ausubel et al., supra). The RNA-positive plants are then analyzed for resistance to Agrobacterium infection and crown gall formation using the methods described above. Transformed grapevines that express a virE2 gene (or virD2 gene) or fragment thereof and have resistance to crown gall disease relative to control plants are taken as being useful in the invention.

All publications and patent applications mentioned in this specification are herein incorporated by reference to the same extent as if each independent publication or patent application was specifically and individually indicated to be incorporated by reference.

What is claimed is:

1. A method for providing resistance to *Agrobacterium vitis* which infects a grapevine or grapevine component, said method comprising the steps of:

(a) transforming grape plant cells with a vir gene or an anti-pathogenic fragment thereof which is expressed in said grape plant cells;

(b) regenerating a transgenic grapevine or transgenic grapevine component from said grape plant cells; and (c) selecting a transgenic grapevine or transgenic grapevine component which expresses said vir gene or said anti-pathogenic fragment thereof, wherein expression of said vir gene or said anti-pathogenic fragment provides resistance to said *Agrobacterium vitis*, wherein said vir gene or said anti-pathogenic fragment thereof is derived from *Agrobacterium vitis* or *Agrobacterium tumefaciens* and is selected from the group consisting of virE2, virD2, virE2 deletion B, virE2 deletion C, and virE2 deletion D.

2. The method of claim 1, wherein said vir gene or said anti-pathogenic fragment thereof is integrated into the genome of the transgenic grapevine or transgenic grapevine component.

3. The method of claim 1, wherein said vir gene is virE2.

4. The method of claim 1, wherein said vir gene is virD2.

5. The method of claim 1, wherein said anti-pathogenic gene fragment is the virE2 deletion B.

6. The method of claim 1, wherein said transgenic grapevine or transgenic grapevine component is a member of the genus Vitis.

7. The method of claim 1, wherein said transgenic grapevine component is a somatic embryo, a scion, or a rootstock.

8. The method of claim 1 wherein said vir gene or said anti-pathogenic fragment thereof is derived from *Agrobacterium vitis*.

9. The method of claim 1 wherein said vir gene or said anti-pathogenic fragment thereof is derived from *Agrobacterium tumefaciens*.

10. The method of claim 1, wherein expression of said vir gene or anti-pathogenic fragment thereof reduces crown gall formation on said transgenic grapevine or transgenic grapevine component.

11. The method of claim 1, wherein said vir gene or an anti-pathogenic fragment thereof is from a Ti plasmid.

12. A transgenic grapevine or transgenic grapevine component transformed with an *Agrobacterium vitis* or *Agrobacterium tumefaciens* vir gene or an anti-pathogenic fragment thereof selected from a group consisting of virE2, virD2, virE2 deletion B, virE2 deletion C, and virE2 deletion D, wherein expression of said vir gene or said anti-pathogenic fragment thereof in said transgenic grapevine or transgenic grapevine component provides resistance to *Agrobacterium vitis*.

13. The transgenic grapevine or transgenic component of claim 12, wherein said vir gene of said anti-pathogenic fragment thereof is integrated into the genome of the transgenic grapevine or transgenic grapevine component.

14. The transgenic grapevine or transgenic grapevine component of claim 12, wherein said vir gene is virE2.

15. The transgenic grapevine or transgenic grapevine component of claim 12, wherein said vir gene is virD2.

16. The transgenic grapevine or transgenic grapevine component of claim 12, wherein said anti-pathogenic gene fragment is the virE2 deletion B.

17. The transgenic grapevine or transgenic grapevine component of claim 12, wherein said grapevine or grapevine component is a member of the genus Vitis.

18. The transgenic grapevine or transgenic grapevine component of claim 12, wherein said grapevine component is a somatic embryo, a scion, or a rootstock.

19. The transgenic grapevine or transgenic grapevine component of claim 12 wherein said vir gene or said anti-pathogenic fragment thereof is derived from *Agrobacterium vitis*.

20. The transgenic grapevine or transgenic grapevine component of claim 12 wherein said vir gene or said anti-pathogenic fragment thereof is derived from *Agrobacterium tumefaciens*.

21. The transgenic grapevine or transgenic grapevine component of claim 12, wherein expression of said vir gene or said anti-pathogenic fragment thereof reduces crown gall formation on said transgenic grapevine or grapevine component.

22. The transgenic grapevine or transgenic grapevine component of claim 12, wherein said vir gene or anti-pathogenic fragment thereof is from a Ti plasmid.

23. The method of claim 1, wherein said anti-pathogenic fragment is virE2 deletion C.

24. The method of claim 1, wherein said anti-pathogenic fragment is virE2 deletion D.

25. The transgenic grapevine or transgenic grapevine component of claim 12, wherein said anti-pathogenic fragment is virE2 deletion C.

26. The transgenic grapevine or transgenic grapevine component of claim 12, wherein said anti-pathogenic fragment is virE2 deletion D.

* * * * *

UNITED STATES PATENT AND TRADEMARK OFFICE
CERTIFICATE OF CORRECTION

PATENT NO.   : 6,172,280 B1
DATED         : January 9, 2001
INVENTOR(S)  : Thomas J. Burr et al.

It is certified that error appears in the above-identified patent and that said Letters Patent is hereby corrected as shown below:

Title page,
Second colum, under "Clare et al." replace "126-127" with -- 126-137 --;

Column 2,
Line 11, replace "Agrobacteriurn's" with -- Agrobacterium's --;
Line 46, replace "Agrobacteriurn" with -- Agrobacterium --;

Column 6,
Line 17, replace "tuniefaciens" with -- tumefaciens --;
Line 62, replace "110OR" with -- 110R --;

Column 7,
Line 2, replace "110OR" with -- 110R --;
Line 67, replace "MRNA" with -- mRNA --;

Column 8,
Line 20, replace "Md." with -- MD --;
Line 62, replace "A. lumefaciens" to -- A. tumefaciens --;
Line 65, replace "A. turnefaciens" with --A. tumefaciens --;

Column 9,
Line 63, replace "A. tuinefaciens" with -- A. tumefaciens --;

Column 12,
Line 37, replace "U.S.A." with -- U.S.A. --;

Column 13,
Line 36, "U.S.A." with -- U.S.A. --;

Column 14,
Line 6, , replace "A. turnefaciens" with --A. tumefaciens --;
Line 12, replace "Telnical Bulletin" with -- Technical Bulletin --;
Line 16, replace "Theor. Appl. Genet." with -- Theor. Appl. Genet. --;

UNITED STATES PATENT AND TRADEMARK OFFICE
CERTIFICATE OF CORRECTION

PATENT NO. : 6,172,280 B1
DATED : January 9, 2001
INVENTOR(S) : Thomas J. Burr et al.

It is certified that error appears in the above-identified patent and that said Letters Patent is hereby corrected as shown below:

Column 15,
Line 2, replace "Femao Pires" with -- Fernao Pires --;

Column 16,
Line 9, replace "constrict" with -- construct --;

Column 18,
Line 25, replace "transgenic component" with -- transgenic grapevine component --.

Signed and Sealed this

Twenty-first Day of May, 2002

*Attest:*

*Attesting Officer*

JAMES E. ROGAN
*Director of the United States Patent and Trademark Office*